United States Patent [19]

Saotome et al.

[11] Patent Number: 4,762,999
[45] Date of Patent: Aug. 9, 1988

[54] RADIATION IMAGE RECORDING AND READ-OUT APPARATUS

[75] Inventors: Shigeru Saotome; Masamitsu Ishida, both of Kanagawa, Japan

[73] Assignee: Fuji Photo Film Co., Ltd., Kanagawa, Japan

[21] Appl. No.: 787,849

[22] Filed: Oct. 16, 1985

[30] Foreign Application Priority Data

Oct. 16, 1984 [JP] Japan .................................. 59-216909
Oct. 20, 1984 [JP] Japan .................................. 59-220741
Oct. 27, 1984 [JP] Japan .................................. 59-226147

[51] Int. Cl.$^4$ ............................................. G03C 5/16
[52] U.S. Cl. ................................... 250/327.2; 378/26
[58] Field of Search ............. 378/26; 250/327.2, 484.1

[56] References Cited

U.S. PATENT DOCUMENTS

| | | | |
|---|---|---|---|
| 4,147,936 | 4/1979 | Eickel | 378/26 |
| 4,543,479 | 9/1985 | Kato | 250/327.2 |
| 4,580,774 | 4/1986 | Yamaguchi et al. | 271/176 |
| 4,581,535 | 4/1986 | Komaki et al. | 250/484.1 |

FOREIGN PATENT DOCUMENTS

| | | |
|---|---|---|
| 0077678 | 4/1983 | European Pat. Off. . |
| 0112203 | 6/1984 | European Pat. Off. ......... 250/327.2 |
| 62-90137 | 4/1987 | Japan . |

Primary Examiner—Carolyn E. Fields
Attorney, Agent, or Firm—Sughrue, Mion, Zinn, Macpeak, and Seas

[57] ABSTRACT

A radiation image recording and read-out apparatus comprises an image recording section, an image reading section, an erasing section, a circulating and conveying means for conveying stimulable phosphor sheets from section to section and a radiation source which is provided opposed to the image recording section spaced therefrom by a predetermined distance. The circulating and conveying means is arranged to convey the stimulable phosphor sheet in the image recording section. The radiation source is arranged to be movable over the object in the image recording section. A motion control mechanism moves the stimulable phosphor sheet and the radiation source relative to each other in the image recording section substantially satisfying a linear law and a geometric law with respect to a desired cross section of the object.

3 Claims, 5 Drawing Sheets

RADIATION IMAGE RECORDING AND READ-OUT APPARATUS

BACKGROUND OF THE INVENTION

1. Field of the Invention

This invention relates to a radiation image recording and read-out apparatus for recording a radiation image of an object on a stimulable phosphor sheet and photoelectrically reading the image recorded on the stimulable phosphor sheet.

2. Description of the Prior Art

When certain kinds of phosphors are exposed to radiation such as X-rays, α-rays, β-rays, γ-rays, cathode rays or ultraviolet rays, they store a part of the energy of the radiation. Then, when the phosphor which has been exposed to the radiation is exposed to stimulating rays such as visible light, light is emitted from the phosphor in the pattern of the stored energy of the radiation. A phosphor exhibiting such properties is referred to as a stimulable phosphor and a sheet material bearing thereon a stimulable phosphor layer is referred to as a "stimulable phosphor sheet" and can be used as a recording medium for recording thereon radiation image information.

As disclosed in U.S. Pat. Nos. 4,258,264, 4,276,473, 4,315,318 and 4,387,428, and Japanese Unexamined Patent Publication No. 56(1981)-11395, it has been proposed to use a stimulable phosphor in a radiation image recording and reproducing system. Specifically, a sheet comprising the stimulable phosphor is first exposed to a radiation passing through an object to have a radiation image stored therein, and is then scanned with stimulating rays which cause it to emit light in proportion to the radiation energy stored. The light emitted from the stimulable phosphor sheet when the sheet is exposed to the stimulating rays is photoelectrically detected and converted to an electric image signal, which is processed as desired to reproduce a visible image having an improved quality, particularly a high diagnostic efficiency and accuracy. The finally obtained visible image may be reproduced in the form of a hard copy or may be displayed on a cathode ray tube (CRT). In this radiation image recording and reproducing system, the stimulable phosphor sheet is used to temporarily store the radiation image in order to reproduce the final visible image therefrom in a final recording medium. For economical reasons, therefore, it is desirable that the stimulable phosphor sheet be used repeatedly.

Further, in a mobile X-ray diagnostic station such as a traveling X-ray diagnostic station in the form of a vehicle like a bus which is provided with a radiation image recording and read-out apparatus for use in the aforesaid radiation image recording and reproducing system and moves from place to place to record radiation images for mass medical examinations, it is disadvantageous to load the mobile X-ray diagnostic station with a large number of stimulable phosphor sheets, and the number of the stimulable phosphor sheets which can be loaded on the mobile X-ray diagnostic station is limited. Therefore, it is desired to load the mobile X-ray diagnostic station with stimulable phosphor sheets which can be used repeatedly, once store the radiation images of the objects in the stimulable phosphor sheets, convey the electric image signals read out from the stimulable phosphor sheets into a recording medium having a large storage capacity, such as a magnetic tape, and circulate and reuse the stimulable phosphor sheets for further image recording and read-out operations, thereby to obtain the radiation image signals of many objects. Further, when image recording is conducted continuously by circulating and reusing the stimulable phosphor sheets, it becomes possible to increase the image recording speed in mass medical examination. This is very advantageous in practical use.

In order to reuse stimulable phosphor sheets as described above, the radiation energy remaining in the stimulable phosphor sheet after it is scanned with stimulating rays to read out the radiation image stored therein should be erased by exposure to light or heat as described, for example, in Japanese Unexamined Patent Publication No. 56(1981)-12599 or U.S. Pat. No. 4,400,619. The stimulable phosphor sheet should then be used again for radiation image recording.

From the aforesaid viewpoint, the applicant proposed in U.S. patent application Ser. No. 600,689 and in Japanese Patent Application No. 58(1983)-66730 a built-in type radiation image recording and read-out apparatus comprising:

(i) a circulating and conveying means for conveying at least one stimulable phosphor sheet for recording a radiation image thereon along a predetermined circulation path, (ii) an image recording section positioned on said circulation path for recording a radiation transmission image of an object on said stimulable phosphor sheet by exposing said stimulable phosphor sheet to a radiation passing through said object, (iii) an image read-out section positioned on said circulation path and provided with a stimulating ray source for emitting stimulating rays for scanning said stimulable phosphor sheet carrying said radiation image stored therein in said image recording section, and a photoelectric read-out means for detecting light emitted from said stimulable phosphor sheet scanned with said stimulating rays to obtain an electric image signal, and (iv) an erasing section for, prior to the next image recording on said stimulable phosphor sheet for which the image read-out has been conducted in said image read-out section, having said stimulable phosphor sheet release the radiation energy remaining in said stimulable phosphor sheet, whereby said stimulable phosphor sheet is circulated through said image recording section, said image read-out section and said erasing section and reused for radiation image recording.

In the aforesaid radiation image recording and read-out apparatus, recording and read-out of radiation images can be conducted continuously and efficiently. The radiation image recording and read-out apparatus of this type will be referred to as a "built-in type radiation image recording and read-out apparatus", hereinbelow.

The built-in type radiation image recording and read-out apparatus is advantageous in various points. For example, when recording a number of people at a mobile X-ray diagnostic station such as a bus equipped with an X-ray image recording apparatus, a number of stimulable phosphor sheets equal to the member of people to be diagnosed must be loaded on the bus if the stimulable phosphor sheets are not repeatedly used. However, only a limited number of stimulable phosphor sheets can be loaded on the bus. This problem can be overcome by repeatedly using the stimulable phosphor sheets and staring the image signals read in the image reading section in a recording medium having a large capacity. Further, by circulating the stimulable phosphor sheets, continuous recording is facilitated and the time required to diagnose a given number of people can be shortened.

There has been known tomographic radiography for obtaining a radiation image of a desired cross section of an object and the stimulable phosphor sheet can be used in tomographic radiography for storing the radiation image of the cross section as disclosed in Japanese Unexamined Patent Publication No. 58(1983)-67245. In tomographic radiography, a radiation source, e.g. an X-ray tube, and a stimulable phosphor sheet are opposed to each other with an object intervening therebetween and are moved, upon activation of the X-ray tube, relative to each other substantially satisfying a linear law (wherein the focal point of the X-ray tube, a point in the desired cross section and a point on the stimulable phosphor sheet are linearly aligned). And a geometric law (wherein the ratio of the distance a between the focal point of the X-ray tube and the desired cross section to the distance b between the desired cross section and the stimulable phosphor sheet is constant). As a result, only an image of the desired cross section of the object is focused on the stimulable phosphor sheet and images of other cross sections of the object are made to be out of focus. In tomographic radiography, the linear law and the geometric law have only to be substantially satisfied, and accordingly, the radiation source and the stimulable phosphor sheet may be moved along various orbits including a linear orbit, a circular orbit, an oval orbit, a hypo-cycloid orbit and a spiral orbit.

However, conventional tomographic radiographic apparatuses are disadvantageous in that they are troublesome to operate and are not adapted to continuous recording since a cassette accommodating therein a stimulable phosphor sheet must be set in the tomographic radiographic apparatus each time recording is effected and must be taken out from the apparatus after recording, and then the stimulable phosphor sheet must be taken out of the cassette in order to read the image information stored therein. Therefore, it would be convenient if said built-in type radiation image recording and read-out apparatus were provided with a tomographic recording function so that tomographic recording, reading and erasure are automatically effected.

SUMMARY OF THE INVENTION

In view of the foregoing observations and description, the primary object of the present invention is to provide a built-in type radiation image recording and read-out apparatus which has a tomographic recording function.

In the built-in type radiation image recording and read-out apparatuses comprising an image recording section, an image reading section, an erasing section, a circulating and conveying means for conveying stimulable phosphor sheets from section to section and a radiation source which is provided opposed to the image recording section spaced therefrom by a predetermined distance, the radiation image recording and read-out apparatus of the present invention is characterized in that the circulating and conveying means is arranged to convey the stimulable phosphor sheet in the image recording section, the radiation source is arranged to be movable over the object to be recorded in the image recording section, and a motion control means is provided for moving the stimulable phosphor sheet and the radiation source relative to each other in the image recording section substantially satisfying said linear law and the geometric law with respect to a desired cross section of the object.

DESCRIPTION OF THE PREFERRED EMBODIMENTS

Figure 1:
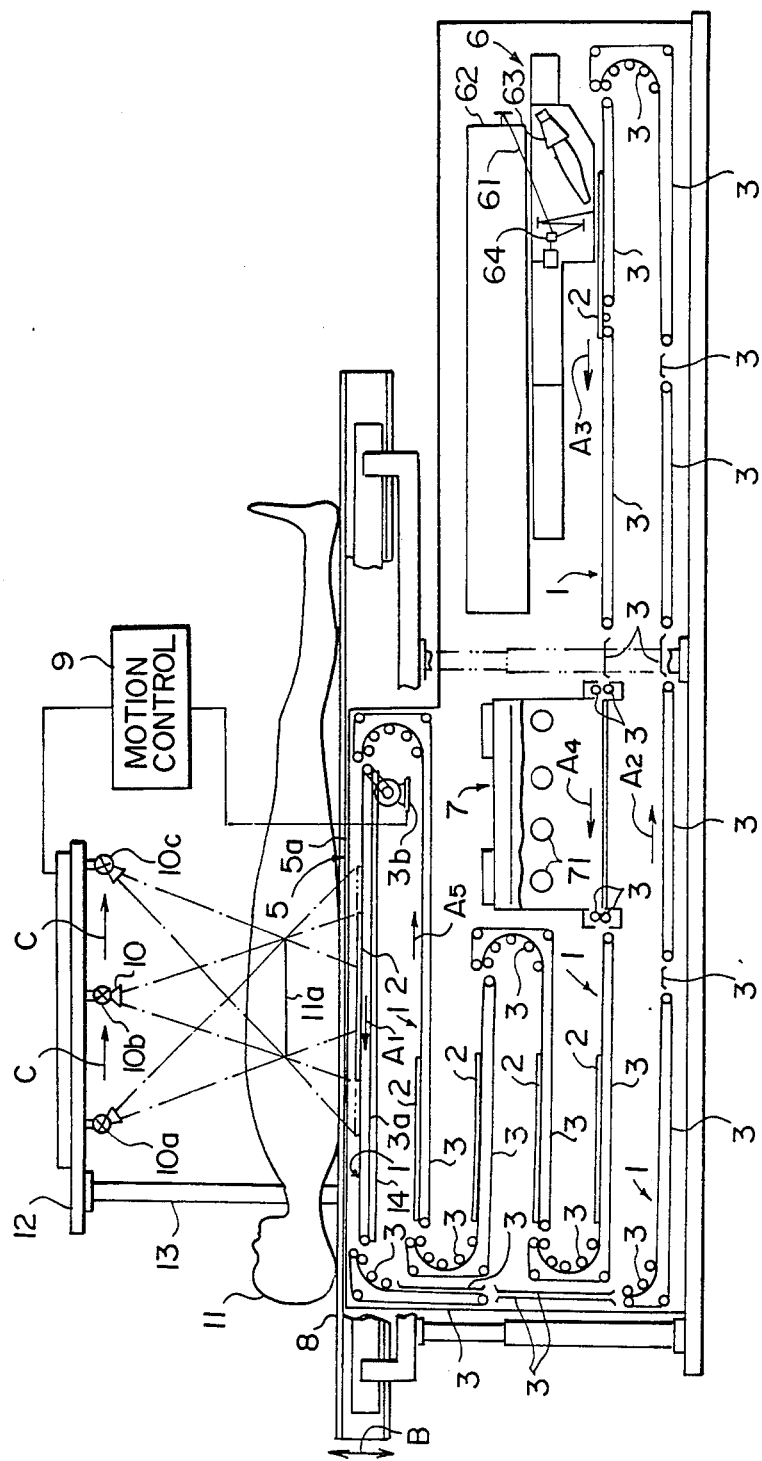
FIG. 1 is a schematic side view showing a radiation image recording and read-out apparatus in accordance with an embodiment of the present invention.

In FIG. 1, in a radiation image recording and read-out apparatus in accordance with an embodiment of the present invention, a circulation path 1 is formed and stimulable phosphor sheets 2 are circulated along the circulation path 1 by a circulating and conveying means 3 comprising rollers, conveyor belts, guide plates and the like.

Along the circulation path 1 are disposed an image recording section 5, an image reading section 6 and an erasing section 7 in this order and the stimulable phosphor sheets 2 are conveyed from section to section in the directions shown by arrows A1 to A5.

In the image recording section 5, each stimulable phosphor sheet 2 is exposed to radiation emitted from a radiation source 10 through an object 11 to record thereon a radiation transmission image of the object 11 as a pattern of the stored radiation energy. After exposure to radiation in the image recording section 5, each stimulable phosphor sheet 2 is conveyed in the direction of the arrows A1 and A2 by the circulating and conveying means 3 to the image reading section 6.

The image reading section 6 comprises a stimulating ray source 62 emitting a stimulating rays 61, which may be a laser beam, a galvanometer mirror 64 for directing the stimulating rays 61 to scan the stimulable phosphor sheet 2, and a photoelectric reading means 63 such as a photomultiplier which receives light emitted from the stimulable phosphor sheet 2 upon exposure to the stimulating rays 61 and converts it into an electrical image signal. The image is read by scanning the stimulable phosphor sheet 2 with the stimulating rays 61 (main scanning) while the stimulable phosphor sheet 2 is conveyed at a constant speed in the direction shown by arrow A3 (sub-scanning). The image signal obtained by the photoelectric reading means 63 is fed to an image processing circuit (not shown) and then fed to an image reproducing system such as a CRT or a recording device for reproducing a radiation transmission image on a photosensitive film by scanning the photosensitive film with a light spot, or a memory for storing the image signal such as a magnetic recording tape.

The stimulable phosphor sheet 2 is subsequently conveyed to the erasing section 7. The erasing section 7 comprises a plurality of erasing light sources 71 which may be fluorescent, tungsten, sodium-vapor, xenon arc, iodine-vapor lamps or the like. By exposing the stimulable phosphor sheet 2 to the light emitted from the erasing light source 71, residual radiation energy in the stimulable phosphor sheet 2 is released.

Then the stimulable phosphor sheet 2 is returned to the image recording section 5.

In the image recording section 5, the circulating and conveying means 3 is in the form of a conveyor belt 3a which is driven by a driving motor 3b and is adapted to linearly move the stimulable phosphor sheet 2 over a predetermined distance. The conveyor belt 3a is provided immediately below a wall portion 5a of the image recording section 5 facing the radiation source 10 and lies parallel to the wall portion 5a at a distance therefrom so that the stimulable phosphor sheet 2 can pass between the wall portion 5a and the conveyor belt 3a. The wall portion 5a is formed of plate material which transmits radiation well and uniformly such as a plastic plate or an aluminum plate. A radiation shield plate 14 made of lead, for instance, is disposed below the conveyor belt 3a. A grid or a Bucky diaphragm including a grid may be disposed between the wall portion 5a and the stimulable phosphor sheet 2 conveyed by the conveyor belt 3a as a scattered radiation removing means. The scattered radiation removing means may extend entirely over said predetermined distance by which the stimulable phosphor sheet 2 is linearly conveyed during tomographic recording. Alternatively, the scattered radiation removing means may have a length substantially equal to or larger than the length of the stimulable phosphor sheet 2 and may be moved along with the stimulable phosphor sheet 2 during tomographic recording.

Immediately above the wall portion 5a is provided an object support plate 8 on which the object is placed. The object support plate 8 extends in parallel to the conveyor belt 3a and the stimulable phosphor sheet 2 conveying direction in the image recording section 5 (i.e., the direction shown by the arrow A1) and is movable up and down perpendicular to the stimulable phosphor sheet conveying direction as shown by arrow B. The object support plate 8 may be moved up and down by a suitable known mechanism comprising a rack-and-pinion, a hydraulic mechanism or the like. Similarly to the wall portion 5a, the object support plate 8 is formed of plate material which transmits radiation well and uniformly.

The object support plate 8 may be further movable in the direction perpendicular to both the directions shown by the arrows A1 and B and may be moved in this direction by a known mechanism.

The radiation source 10 is disposed a predetermined distance above the image recording section 5 and is linearly movable over a predetermined distance in a direction parallel to the stimulable phosphor sheet conveying direction in the image recording section 5. More specifically, a base plate 12 is supported on a supporting post 13 fixed to the image recording section 5 so that the lower surface of the base plate 12 extends in parallel to the surface along which the stimulable phosphor sheet 2 is conveyed in the image recording section 5, and the radiation source 10 is mounted on the base plate 12 to be linearly movable along the lower surface of the base plate 12. More particularly, a screw rod (not shown) is mounted on the lower surface of the base plate 12 to extend in a direction parallel to the stimulable phosphor sheet conveying direction and the radiation source 10 is screw-engaged with the screw rod while being restrained so as not to be rotatable with respect thereto. Other various mechanisms may be employed to support the radiation source 10 so as to be linearly movable in parallel to the stimulable phosphor sheet conveying direction. For example, a guide groove extending in a direction may be formed on the lower surface of the base plate 12 and the radiation source 10 be engaged with the guide groove to be slidable therealong. In this casse, a chain is connected to the radiation source 10 and the chain is driven by way of a sprocket.

The linear movement of the stimulable phosphor sheet 2 in the image recording section 5 and the linear movement of the radiation source 10 are controlled by a motion control means 9 so that the stimulable phosphor sheet 2 and the radiation source 10 move relative to each other in the image recording section substantially satisfying said linear law and the geometric law with respect to a desired cross section 11a of the object 11. In this particular embodiment, the motion control means 9 inputs driving signals into the driving motor 3b for driving the conveyor belt 3a and the driving motors for driving the screw rod on which the radiation source 10 is mounted which driving signals control the driving motors so that the stimulable phosphor sheet 2 and the radiation source 10 are moved in opposite directions maintaining a predetermined speed ratio suitable for substantially satisfying said linear law and the geometric law. Thus, tomographic recording is effected while the stimulable phosphor sheet 2 is conveyed in the direction of the arrow A1 and the radiation source 10 is moved in the direction of arrows 10a, 10b and 10c satisfying the linear law and the geometric law.

Now another embodiment of the present invention will be described in detail with reference to FIGS. 2 to 6.

Figure 2:
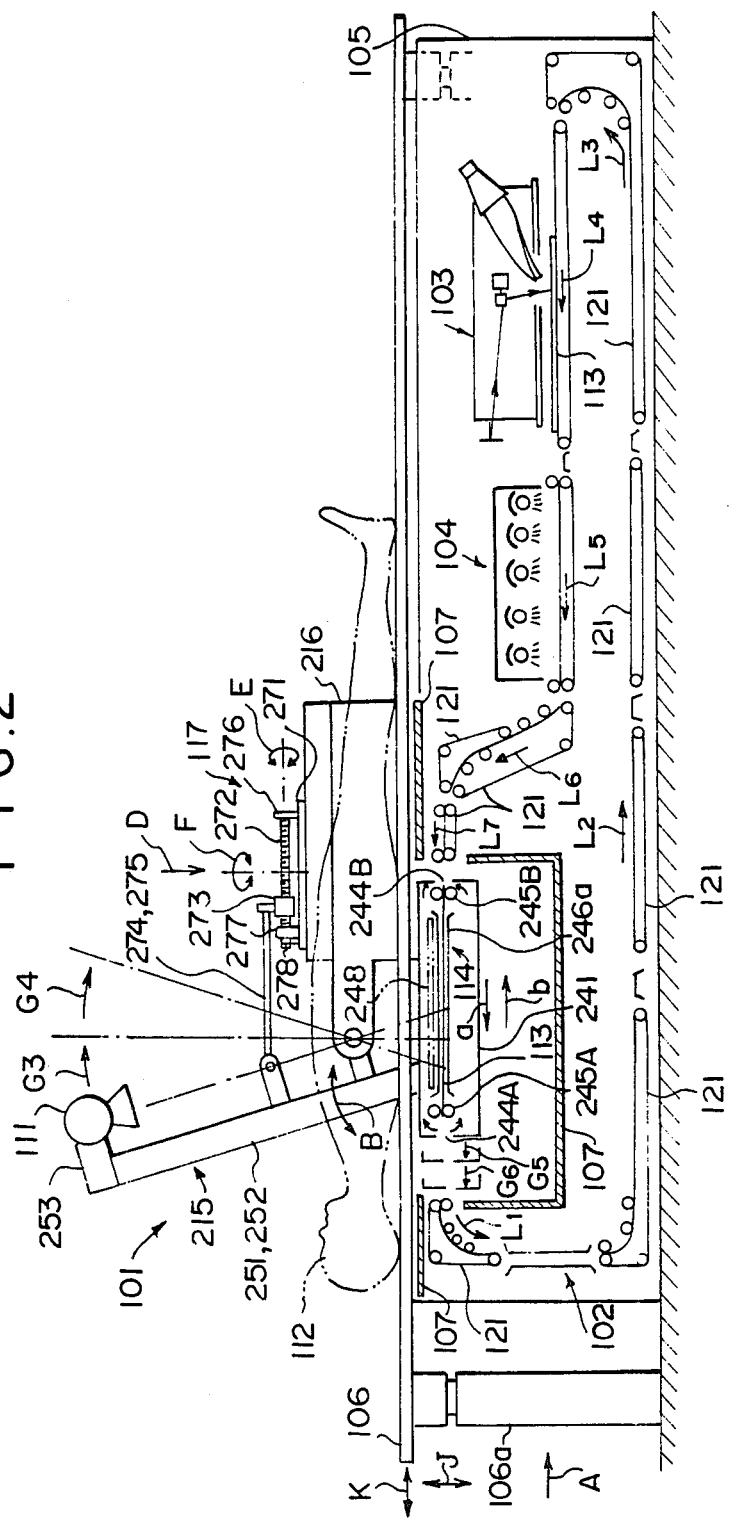
FIG. 2 is a view similar to FIG. 1 but showing a radiation image recording and read-out apparatus in accordance with another embodiment of the present invention.

In FIG. 2, a circulation path 102 is formed in a light shield housing 105. Stimulable phosphor sheets 113 are conveyed along the circulation path 102 by a circulating and conveying means 121 which may comprise rollers, conveyor belts and the like. Along the circulation path 102, there are provided an image recording section 101, an image reading section 103 and an erasing section 104. The stimulable phosphor sheets 113 are conveyed from section to section along the circulation path 102 by the circulating and conveying means 121 as indicated by arrows L1 to L7.

The image recording section 101 comprises a radiation source 111 and a stimulable phosphor sheet holder 114 for holding the stimulable phosphor sheet 113 in a recording position in which the stimulable phosphor sheet 113 is exposed to radiation emitted from the radiation source 111 and passing through an object 112, thereby recording a radiation image of the object 112 on the stimulable phosphor sheet 113. The stimulable phosphor sheet holder 114 comprises a guide plate system 246, and two pairs of conveyor rollers 245A and 245B on the respective ends of the guide plate system 246 which form a part of the circulating and conveying means 121, and is held by a housing 241. The relative position of the stimulable phosphor sheet 113, the guide plate system 246 and conveyor rollers 245A and 245B is clearly shown in FIG. 6. The guide plate system 246 comprises a lower plate member 246a having a width substantially equal to the width of the stimulable phosphor sheet 113 and a pair of upper plate members 246b which are narrower than the stimulable phosphor sheet 113 and are spaced from each other in the direction of the width of the stimulable phosphor sheet 113. The stimulable phosphor sheet 113 is passed between the upper and lower plate members 246a and 246b. Preferably, the guide plate system 246 is formed of lead, iron or the like in order to prevent backscattering to the stimulable phosphor sheet 113.

The stimulable phosphor sheet holder 114 and the radiation source 111 are arranged to be movable relative to each other substantially satisfying said linear law and the geometric law with respect to a desired cross section 12a (FIG. 3) of the object. The stimulable phosphor sheet holder 114 is moved together with the housing 241.

Figure 3:
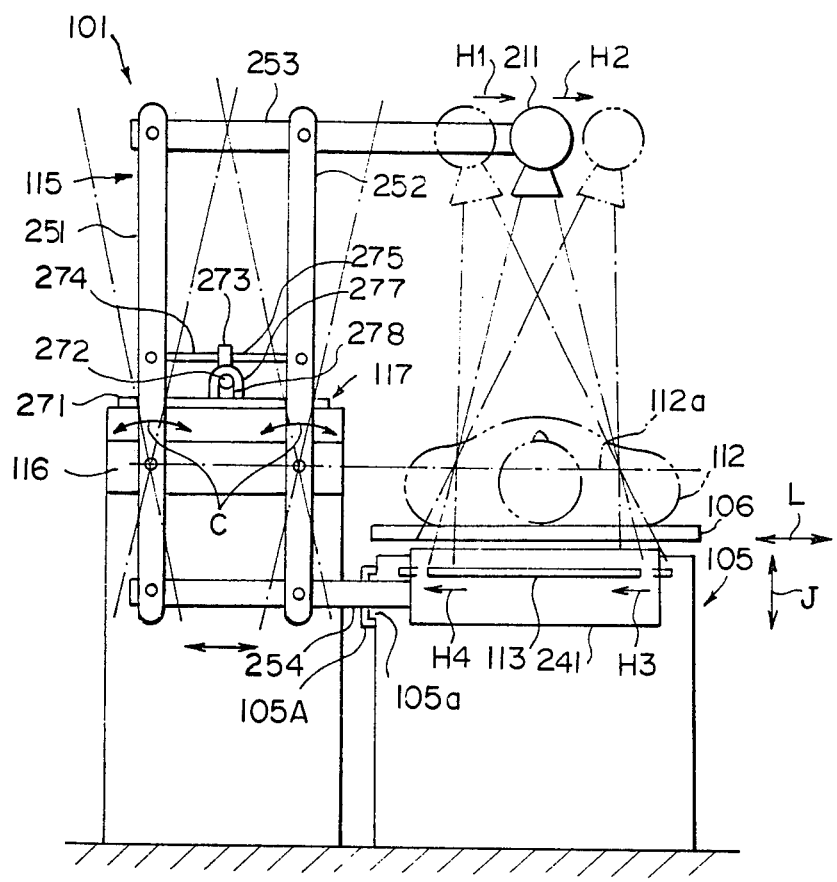
FIG. 3 is a schematic front view of the radiation image recording and read-out apparatus of FIG. 2.
Figure 4:
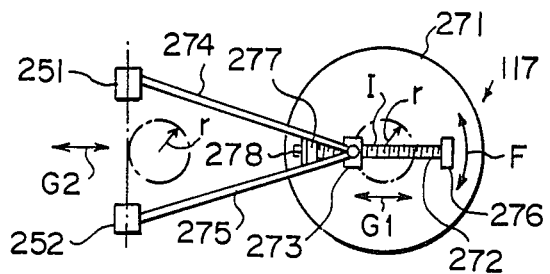
FIG. 4 is a plan view showing a part of the radiation image recording and read-out apparatus of FIG. 2.
Figure 5:
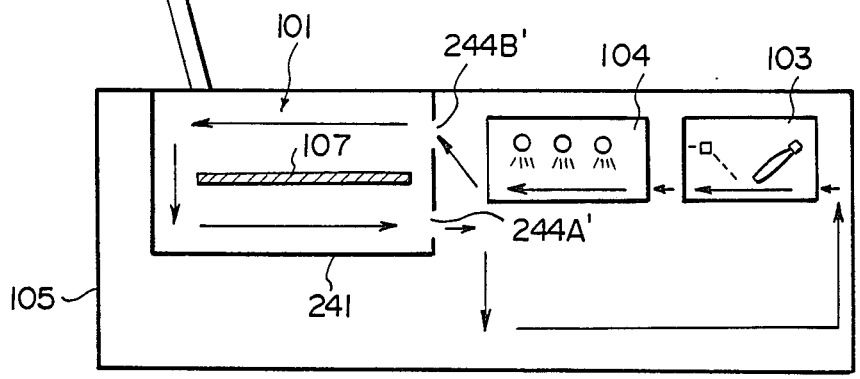
FIG. 5 is a schematic view for illustrating a modification of the embodiment of FIG. 2.
Figure 6:
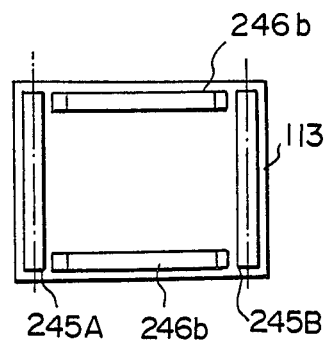
FIG. 6 is a plan view of the stimulable phosphor sheet holder employed in the radiation image recording and read-out apparatus of FIG. 2.

The housing 241 and the radiation source 111 are connected by way of a connecting means 115 comprising a parallel linkage. The connecting means 115 comprises a pair of parallel vertical rods 251 and 252, an upper transverse rod 253 connected to the upper end portions of the vertical rods 251 and 252, and a lower transverse rod 254 connected to lower end portions of the vertical rods 251 and 252. The radiation source 111 is supported on the upper transverse rod 253 and the housing 241 accommodating therein the stimulable phosphor sheet holder 114 is supported on the lower transverse rod 254. The vertical rods 251 and 252 are mounted on a base 116 at intermediate portions between the transverse rods 253 and 254 for swinging motion in both the directions of arrows B (FIG. 2) and C (FIG. 3). The vertical rods 251 and 252 are connected to a driving means 117. As shown in FIGS. 2 to 4, the driving means 117 comprises a rotary table 271 mounted on the base 116, a male screw rod 272 mounted on the rotary table 271, a female screw member 273 screwed on the male screw rod 272, a first connecting rod 274 connected to the female screw member 273 at one end and to the vertical rod 251 at the other end, and a second connecting rod 275 connected to the female screw member 273 at one end and to the vertical rod 252 at the other end. The male screw rod 272 is supported for axial rotation (as indicated by arrow E) on a pair of bearings 276 and 277 fixedly mounted on the rotary table 271, and is driven by an electric motor (not shown) by way of a chain 278. The male screw rod 272 can be rotated about the axis of the rotary table 271 together with the rotary table 271 as indicated by arrow F.

The triangle formed by the connecting rods 274 and 275 connecting the female screw member 273 and the vertical rods 251 and 252, that is, the triangle having its three apices respectively on the female screw member 273 and the vertical rods 251 and 252, cannot be deformed. Accordingly, as shown in FIG. 4, when the rotary table 271 is fixed and the male screw rod 272 is rotated, the female screw member 273 is linearly moved in the direction of arrow G1 and the connecting means 115 is linearly moved in the direction of arrow G2, whereby the radiation source 111 is moved in the direction indicated by arrows G3 and G4 (FIG. 2), and the housing 241, accordingly the stimulable phosphor sheet 113 is moved in the direction indicated by arrows G5 and G6 satisfying said linear law and the geometric law. Thus so-called linear orbit tomographic recording can be effected. When the rotary table 271 is rotated by 90° from the position shown in FIG. 3 and the male screw rod 272 is rotated, the radiation source 111 is moved in the direction of arrows H1 and H2 and the housing 241 is moved in the direction of arrows H3 and H4, whereby linear orbit tomographic recording in this direction can be effected. Further, when the female screw member 273 is positioned at a distance r from the center of the rotary table 271 as shown in FIG. 4 and the rotary table 271 is rotated, the female member 273 is moved on a circle having a radius of r and the connecting means 115 is also moved on a circle having a radius of r, whereby circular orbit tomographic recording can be effected. Further, by combining rotation of the male screw rod 272 in the direction of the arrow E and the rotation of the rotary table 271 in the direction of the arrow F, various type tomographic recording such as spiral orbit tomographic recording can be effected.

A Bucky diaphragm 148 is mounted on the stimulable phosphor sheet holder 114. It is possible to arrange the grid of the Bucky diaphragm 148 to rotate when the circular orbit tomographic recording is effected.

The object 112 is placed on a support table 106 having telescopic legs 106a. The support table 106 is movable up and down in the direction of arrow J by a known mechanism such as a rack-and-pinion mechanism, a hydraulic mechanism or the like so that the cross section 112a of the object 112 to be radiographed can be changed. The support table 106 may be arranged to be horizontally movable in the directions of arrows K and L. As shown in FIG. 3, said lower transverse rod 254 extends through an opening 105a formed in the light shield housing 105 and is connected to the housing 241 accommodating therein the stimulable phosphor sheet holder 114. The opening 105a has a size sufficient to permit movement of the lower transverse rod 254 described above. A light shield cover 105A formed of flexible material such as cloth closes the opening 105a in order to prevent ambient light from entering the housing interior.

After recording in the image recording section 101, the housing 241 is moved in the direction of arrow a so that the stimulable phosphor sheet holder 114 is connected to the circulating and conveying means 121 disposed on the left side of the housing 241 as seen in FIG. 2. Then the conveyor rollers 245A are rotated in the directions of the arrows to discharge the stimulable phosphor sheet 113 from the image recording section 101 through an outlet opening 244A formed in the housing 241. Thereafter the stimulable phosphor sheet 113 is conveyed to the image reading section 103 along the circulation path 102 as indicated by the arrows L1, L2 and L3. Radiation shield plates 107 (which may be of lead, for instance) are disposed between the image recording section 101 and the circulation path 102 below and beside the image recording section 101 in the light shield housing 105 in order to prevent the stimulable phosphor sheet 113 conveyed along the circulation path 102 from being exposed to radiation emitted from the radiation source 111. When no stimulable phosphor sheet 113 exists below and beside the image recording section 101 upon emission of radiation from the radiation source 111, the shield plates 107 may be omitted.

From the image reading section 103, the stimulable phosphor sheet 113 is returned to the image recording section 101 by way of the erasing section 104. The image reading section 103 and the erasing section 104 are substantially the same as the image reading section 6 and the erasing section 7 of the embodiment shown in FIG. 1, and accordingly will not be described in detail here.

When the stimulable phosphor sheet 113 is conveyed to the image recording section 101 after erasure, the housing 241 is moved in the direction of arrow b so that the stimulable phosphor sheet holder 114 is connected to the circulation means 121 on the right side of the housing 241 as seen in FIG. 2. Then the conveyor rollers 245B are rotated in the directions of the arrows to introduce the stimulable phosphor sheet 113 into the housing 241 through an inlet opening 244B formed in the housing 241. After introduction of the stimulable phosphor sheet 113 into the image recording section 101, the housing 241 is moved in the direction of the arrow a, when required, to a position suitable for beginning the desired recording. After recording, the housing 241 is again moved in the direction of the arrow a to discharge the stimulable phosphor sheet 113 from the image recording section 101 as described above.

The positions of the respective sections is not limited to those shown in FIG. 2. For example, the outlet opening and the inlet opening of the housing 241 may be formed on the same side of the housing 241 as indicated at 244A' and 244B' in FIG. 5 so that the stimulable phosphor sheet 113 is caused to U-turn in the housing 241 and is discharged from the outlet opening 244A'.

Now still another embodiment of the present invention will be described with reference to FIGS. 7 and 8.

The radiation image recording and read-out apparatus of this embodiment is substantially the same as that shown in FIG. 2 except that the circulation means somewhat differs from that in the embodiment shown in FIG. 2. Accordingly, the parts analogous to the parts shown in FIG. 2 are given the same reference numerals and will not be described in detail here.

Figure 7:
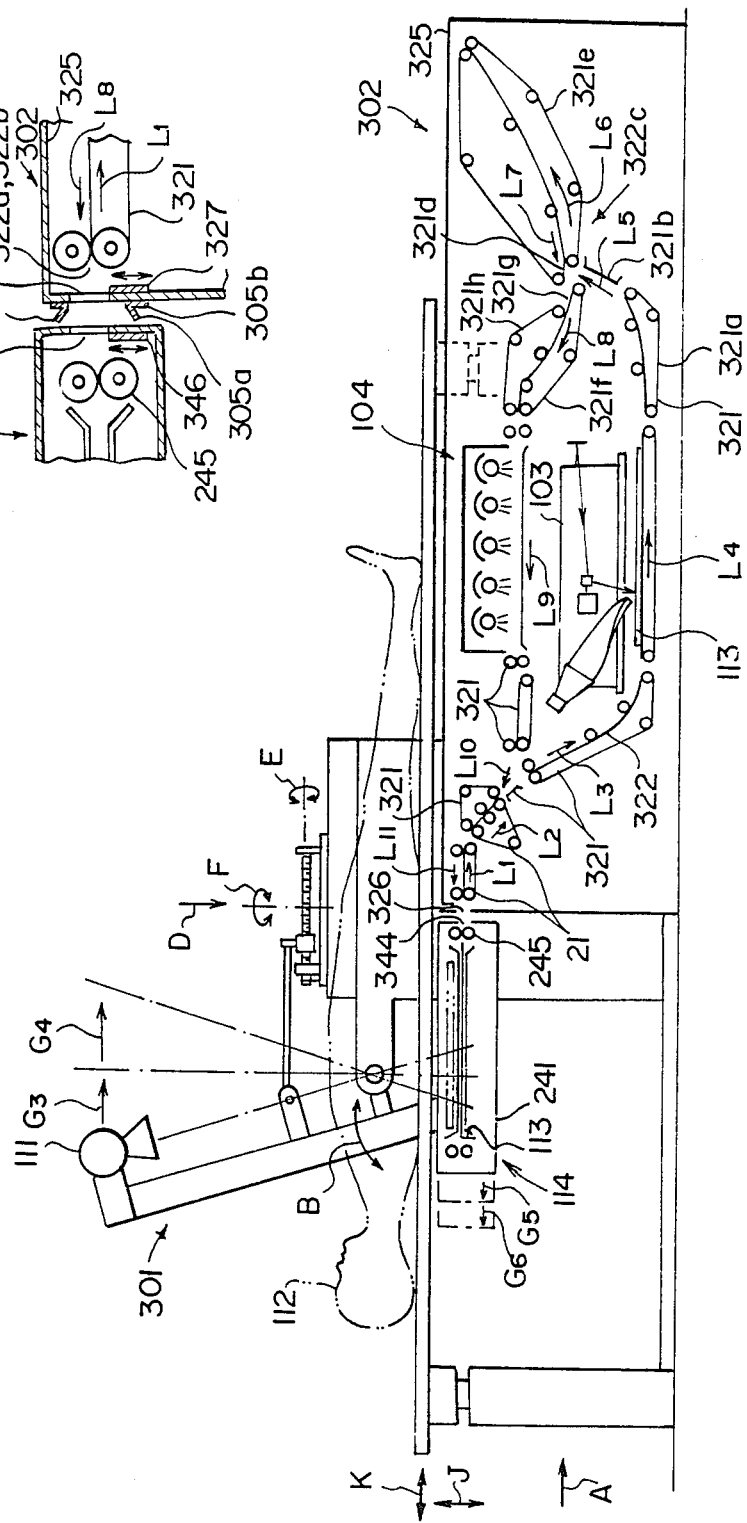
FIG. 7 is a view similar to FIG. 2 but shows still another embodiment of the present invention.

In FIG. 7, the radiation image recording and readout apparatus of this embodiment comprises a tomographic recording system 301 and a reading and erasing system 302. In the reading and erasing system 302 is formed a path 322 along which the stimulable phosphor sheets 113 are conveyed by a conveying means 321 in the directions indicated by arrows L1 to L11. Along the path 322 are disposed the image reading section 103 and the erasing section 104. The portion of the path 322 between the image reading section 103 and the erasing section 104 is provided in the form of a switchback path 322c. In the switchback path 322c, the stimulable phosphor sheet 113 is conveyed by a first conveyor belt 321a and a guide plate 321b in the direction of the arrow L5. When the leading edge of the stimulable phosphor sheet 113 abuts against an end portion 321d of a second conveyor belt 321c, the stimulable phosphor sheet 113 is conveyed by the second conveyor belt 321c and a third conveyor belt 321e in the direction of the arrow L6. When the stimulable phosphor sheet 113 is entirely fed between the second and third conveyor belts 321c and 321e, the conveyor belts 321c and 321e are moved in the reverse direction to convey the stimulable phosphor sheet 113 in the direction of the arrow L7. Thereby, the rear edge of the stimulable phosphor sheet 113 is brought into contact with a receiving portion 321g of a fourth conveyor belt 321f, and the stimulable phosphor sheet 113 is conveyed by the fourth conveyor belt 321f and a fifth conveyor belt 321h in the direction of the arrow L8 to be introduced into the erasing section 104. The reason why the stimulable phosphor sheet 113 is conveyed in the switchback fashion is to keep the same surface of the stimulable phosphor sheet 113 facing upward in both the image reading section 103 and the erasing section 104.

The stimulable phosphor sheet 113 is conveyed in the direction of the arrows L9 to L11 after erasure.

Figure 8:
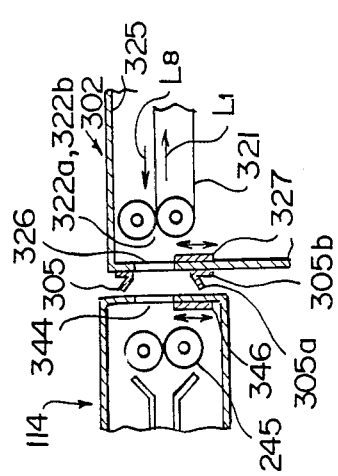
FIG. 8 is an enlarged fragmentary cross-sectional view showing a part of the radiation image recording and read-out apparatus of FIG. 7.

As shown in FIG. 8, the starting end 322a of the path 322 which also forms the terminating end 322b of the same is opposed to a communicating opening 326 formed in a housing 325 of the reading and erasing system 302. The starting end 322a of the path 322 is disposed upstream of the image reading section 103 with respect to the stimulable phosphor sheet conveying direction and the terminating end 322b of the same is disposed downstream of the erasing section 104. The communicating opening 326 is opened and closed by a shutter 327.

The housing 241 for accommodating therein the stimulable phosphor sheet holder 113 is provided with a communicating opening 344 which is provided with a shutter 346. A light shield pipe 305 is fixed to the housing 241 at one end 305a to surround the communicating hole 344. The light shield pipe 305 is made of a diaphragm pipe, for instance, and is contractible. The other end 305b of the light shield pipe 305 is adapted to abut against the housing 325 of the reading and erasing system around the communicating opening 326 when the stimulable phosphor sheet holder 114 is in a sheet receiving and delivering position to be described later.

The reading and erasing system 302 is stationary and the stimulable phosphor sheet holder 114 is movable. When the stimulable phosphor sheet holder 114 is in a predetermined position (the sheet receiving and delivering position), the communicating openings 344 and 326 of the stimulable phosphor sheet holder 114 and the reading and erasing system 302 are opposed to each other so that the stimulable phosphor sheet 113 can be delivered from one of the stimulable phosphor sheet holder 114 and the reading and erasing system 302 to the other through the communicating openings 344 and 326 by the conveying means 321 and the conveyor rollers 245.

The tomographic recording is effected while the stimulable phosphor sheet 113 held by the stimulable phosphor sheet holder 114 and the radiation source 111 are moved relative to each other as described above. After the tomographic recording, the stimulable phosphor sheet holder 114 is moved to the receiving and delivering position. In this position, said the other end 305b of the light shield pipe 305 abuts against the housing 325 of the reading and erasing system 302 to prevent light from entering through the communicating openings 344 and 326, and the shutters 344 and 326 are opened. Then the stimulable phosphor sheet 113 is delivered to the conveying means 321 through the communicating openings 344 and 326. Thus, the stimulable phosphor sheet 113 is conveyed to the image reading section 103 and then to the erasing section 104.

We claim:

1. A radiation image information recording and read-out apparatus comprising:
   a circulating and conveying means for conveying stimulable phosphor sheets along a predetermined circulation path,
   an image recording section which is disposed in the circulation path and in which a radiation image of an object is recorded on each of the stimulable phosphor sheets by exposing the stimulable phosphor sheets to a radiation passing through the object, an image read-out section including a stimulating ray source which is disposed in the circulation path and emits stimulating rays for scanning the stimulable phosphor sheet and a photoelectric read-out means which receives light emitted from the stimulable phosphor sheet to obtain an electric image signal, an erasing section which disposed in the circulation path and releases residual radiation energy in the stimulable phosphor sheet before the stimulable phosphor sheet is returned to the image read-out section, and a radiation source which emits said radiation and is provided opposed to the image recording section spaced therefrom by a predetermined distance, characterized in that said image recording section is provided with a transport means comprising a shuttle means which includes a sheet holding means for holding said stimulable phosphor sheet in fixed position relative thereto, said shuttle means being movable between at least one position where said shuttle means is connected with the circulation path formed by said circulating and conveying means and further positions free from said circulation path, while the stimulable phosphor sheet held thereby receives radiation from said radiation source, and motion control means for controlling relative movement between the shuttle means, when at said further positions, and said radiation source in said recording section so as to substantially satisfy the linear law and the geometric law with respect to a desired cross section of the object.

2. A radiation image recording and read-out apparatus as defined in claim 1 wherein said shuttle means is movable from a first position where a receiving end of said shuttle means is connected to a feed-out end of said circulating and conveying means to a second position where a feed-out end of said shuttle means is connected to a receiving end of said circulating and conveying means, and is movable between said first position and said second position under the control of said motion control means, said feed-out end and receiving end of said circulating and conveying means being separated from each other to provide a distance therebetween through which said shuttle means is moved by said motion control means.

3. A radiation image recording and read-out apparatus as defined in claim 1 wherein said shuttle means comprises a reciprocally movable housing having an opening at only one end thereof, said shuttle means receiving stimulable phosphor sheets from said circulation path at said position where said shuttle means is connected with said circulation path; said shuttle means, after receiving a stimulable phosphor sheet, moving away from said circulation path, under the control of said motion control means, in order to effect recording; and said shuttle means feeding out said stimulable phosphor sheet upon returning to said position where said shuttle means is connected with said circulation path.

* * * * *